United States Patent [19]

Reif

[11] Patent Number: 5,064,432
[45] Date of Patent: Nov. 12, 1991

[54] BICURVED LEAFLET(S) PROSTHETIC HEART VALVE

[75] Inventor: Thomas H. Reif, Milton, Fla.

[73] Assignee: Republic Medical Products Inc., Milton, Fla.

[21] Appl. No.: 529,200

[22] Filed: May 25, 1990

Related U.S. Application Data

[62] Division of Ser. No. 375,253, Jun. 30, 1989, Pat. No. 4,950,287.

[51] Int. Cl.$^5$ .................................................. A61F 2/24
[52] U.S. Cl. ........................................................ 623/2
[58] Field of Search ............................................ 623/2

[56] References Cited

U.S. PATENT DOCUMENTS

| | | | |
|---|---|---|---|
| Re. 31,040 | 9/1982 | Possis | 623/2 |
| 4,240,161 | 12/1980 | Huffstutler, Jr. et al. | 623/2 |
| 4,276,658 | 7/1981 | Hanson et al. | 623/2 |
| 4,775,378 | 10/1988 | Knoch et al. | 623/2 |
| 4,799,930 | 1/1989 | Knoch et al. | 623/2 |
| 4,846,830 | 7/1989 | Knoch et al. | 623/2 |

*Primary Examiner*—Randy C. Shay
*Attorney, Agent, or Firm*—Albert H. Reuther

[57] ABSTRACT

A mechanical artificial heart valve is provided and consists of an annular shaped orifice, to which a single (or multiple) bicurved leaflet(s) is (are) hinged. The curves are planar and are generated from two intersecting circular arcs. The valve is constructed to cause a predominately accelerating flow through the orifice. This significantly reduces the flow separation from the leaflets. In addition, the leaflets are shaped so as to reduce the closing reflux volume through the orifice during the regurgitation phase of flow. These improvements tend to significantly decrease the work load on the heart.

4 Claims, 2 Drawing Sheets

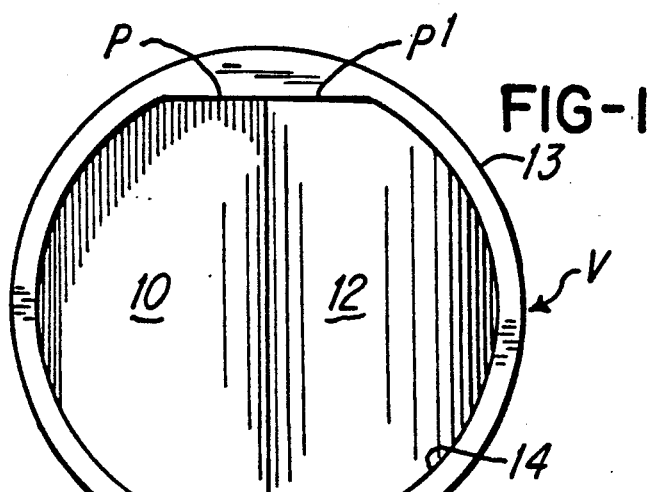
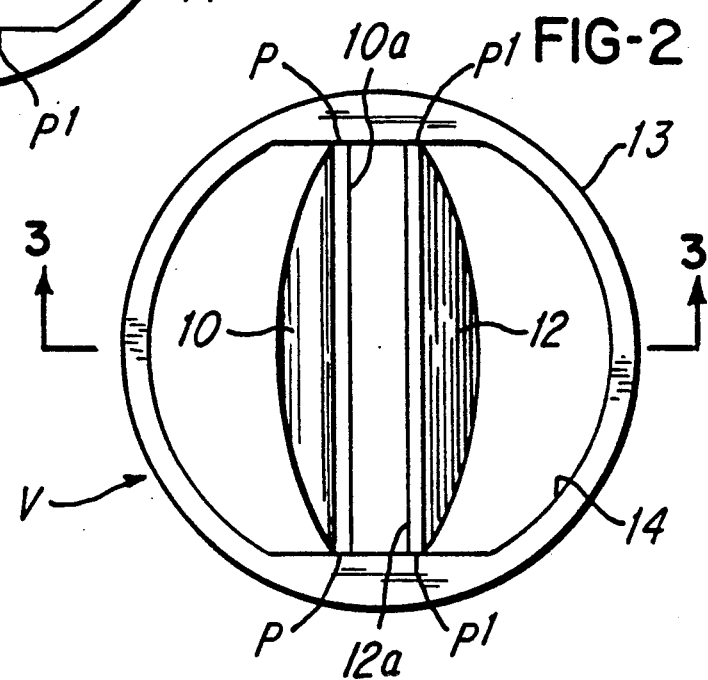
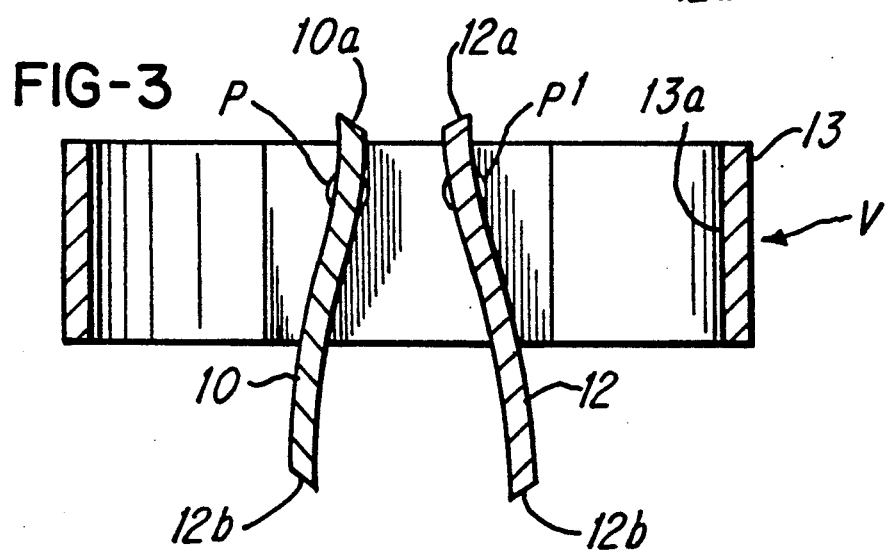

BICURVED LEAFLET(S) PROSTHETIC HEART VALVE

This is a divisional application based on allowed parent co-pending application U.S. Ser. No. 375,253-Reif filed June 30, 1989, now U.S. Pat. No. 4,950,287 and belonging to the assignee of the present invention.

BACKGROUND OF THE INVENTION

1. Field of the Invention

The present invention pertains to an artificial heart valve, and, more particularly, pertains to a mechanical artificial heart valve for use in humans.

2. Description of the Prior Art

There are two basic types of artificial heart valves, biological and mechanical. The medical indications for heart valve replacement are the same for both types. Examples include calcified, congenitally bicuspid aortic valves, rheumatic valvular disease, and rupture of a chordae tendinea.

Biological valves are either harvested from animals, such as pigs (porcine valves) or constructed from animal parts, such as cow pericardium (bovine valves). The primary advantage of these valves is that they do not require long term anticoagulation therapy with drugs like warfarin. These valves are used frequently in situations where anticoagulants are contraindicated, such as pregnant patients, or when medical follow-up may be tedious, such as in underdeveloped countries.

Mechanical valves are made of materials, such as pyrolitic carbon and titanium. In general, mechanical valves are very durable, with service lives expected to exceed the life expectancy of the patient. All mechanical valves in current use require anticoagulation. And, if there are no contraindications to such medications, mechanical heart valves are usually preferred by most physicians.

The mechanical valves commercially available at present, for example, are based on disclosures in U.S Pat. No. 4,276,658-Hanson et al dated July 7 1981; U.S. Pat. No. Re. 31,040-Possis dated Sept. 28, 1982; and U.S. Pat. No. 4,689,046-Bokros et al dated Aug. 25, 1987. All of these mechanical valves utilize the same essential features. That is, they consist of an orifice (an annular shaped frame) with one or more flat leaflets, which are free to rotate, within certain limitations, within the orifice. The restrained motion of these leaflets causes the flow through the orifice to be essentially unidirectional, which mimics the natural function of normal (native) heart valves.

The unidirectional flow characteristic is the primary function of a heart valve, both native and mechanical. Native valves, however, have evolved to a form that also minimizes the work load on the heart. This is accomplished by streamlining the shape of the leaflets to minimize the amount of turbulence (separation of flow) in the wake of the leaflets and to minimize the amount of backflow (regurgitation) during the closure of the leaflets.

Flat leaflets are inherently subject to increased separation effects and, therefore, lead to wasted energy and extra work load on the heart. This has been disclosed in an article "Design Considerations for the Omniscience Pivoting Disc Prosthetic Heart Valve" by Dr. Thomas H. Reif in the International Journal of Artificial Organs (1983), vol. 6, no. 3, pp. 131-138. This article demonstrated that separation effects increase as the degree of opening of the leaflet(s) decreases. The opening angle is mathematically defined by an increase in the angle of attack. It was further demonstrated that these separation effects could be reduced, when compared to flat leaflets at the same angle of attack, by using a curved leaflet with the leading edge (during the forward flow phase) parallel to the flow at the inlet of the orifice. A single curved leaflet mechanical valve disclosed in U.S. Pat. No. 4,240,161-Huffstutler et al dated Dec. 23, 1980, is based on this concept. Such a configuration does improve separation effects, however, it does not eliminate them. Furthermore, the outlet flow is malaligned due to the curvature at the trailing edge.

U.S. Pat. No. 4,775,378-Knock et al dated Oct. 4, 1988, discloses a further improvement of this concept by utilizing an S-shaped leaflet. In this configuration both the leading and trailing edges of the leaflets are aligned parallel to the forward flow. Little attention was given to separation effects, as the chord of the leading edge airfoil is longer than the chord of the trailing edge airfoil Dr. Hermann Schlichting discloses in his text Boundary-Layer Theory, 7th ed., McGraw-Hill Co., New York, 1979, pp. 168-173, that the flow over right circular cylinders rapidly separates on the side of the adverse pressure gradient (region of decelerating flow). Also, this effect is strongly dependent on the ratio of inertia to viscous effects (mathematically defined as the Reynolds number). That is, the separation effects being less important at Reynolds numbers (based on the radius of the cylinder) of greater than $3 \times 10^5$. Physiological flows, however, rarely develop Reynolds numbers (based on the approximate radius of curvature of the leading edge airfoil in excess of $1.5 \times 10^4$. Thus, separation effects are of great importance. Configuring the leaflets, such that the ratio of the chord of the leading edge airfoil is greater than one (1) is not desirable. This is because sufficient time is given for the fluid particles to separate from the leaflet prior to the change in curvature.

All mechanical heart valves have a certain amount of backflow or regurgitation. This regurgitation can be broken down into two components, during each cardiac cycle. One component is the closing reflux volume, which occurs as the leaflets close and sweep some of the fluid through the orifice in the direction opposite to the forward flow. It is an elementary task, using the Theorem of Pappus, to show that the closing reflux volume is proportional to the angle of attack. As the angle of attack becomes smaller, the closing reflux volume must increase. Further, slight modifications in the shape of the leaflets can significantly influence the closing reflux Volume. Leaflets which are not planar may protrude into the orifice, so as to further reduce the closing reflux volume. The valve disclosed by U.S. Pat. No. 4,775,378-Knock dated Oct. 4, 1988, has such a feature. However, because the ratio of the chord of the leading edge airfoil to the chord of the trailing edge airfoil is greater than one (1), this effect is minimized.

The second component of regurgitation is leakage, which occurs because of the imperfect seal between the leaflets and the orifice, when the leaflets are in the closed position. Differences in the regurgitation characteristics of mechanical heart valves have long been noted. However, these differences have generally been accepted as consequences of the angle of attack of the leaflets and the size of the clearance space between the leaflets and the orifice.

In summary, there are several disadvantages to the current or prior art design configuration of the leaflets of mechanical heart valves. All designs demonstrate marked separation effects and at least some regurgitation. Both of these factors lead to increased work load on the heart, as easily demonstrated by fundamental principles of fluid mechanics.

SUMMARY OF THE INVENTION

An object of the present invention is to provide a mechanical heart valve that overcomes these deficiencies of the prior art to a significant degree and to provide this valve as a prosthesis that significantly reduces the effects of separation, reduces the closing reflux or regurgitation volume, and is easily manufactured, as the leaflets are generated from two intersecting, simple circular arcs.

Also, a principal object hereof is to provide a mechanical heart valve for implantation in humans.

A further object of the present invention is to provide a mechanical heart valve that can be stocked in different sizes.

BRIEF DESCRIPTION OF THE DRAWINGS

These as well as other objects and advantages of the present invention will appear more clearly from the following specification in conjunction with the accompanying drawings. Many of the attendant advantages of this invention will be readily appreciated as the same becomes better understood by reference to the following detailed description when considered in connection with the accompanying drawings, in which like reference numerals designate like parts throughout the figures thereof and in which:

FIG. 1 shows a top or inflow view of the prosthetic heart valve with the leaflets in the fully closed position;

FIG. 2 shows a top or inflow view of the prosthetic heart valve with the leaflets in the fully open position;

FIG. 3 shows a cross-sectional view of the prosthetic heart valve taken along line 3—3 as shown in FIG. 2;

DESCRIPTION OF PREFERRED EMBODIMENTS

Figure 4:
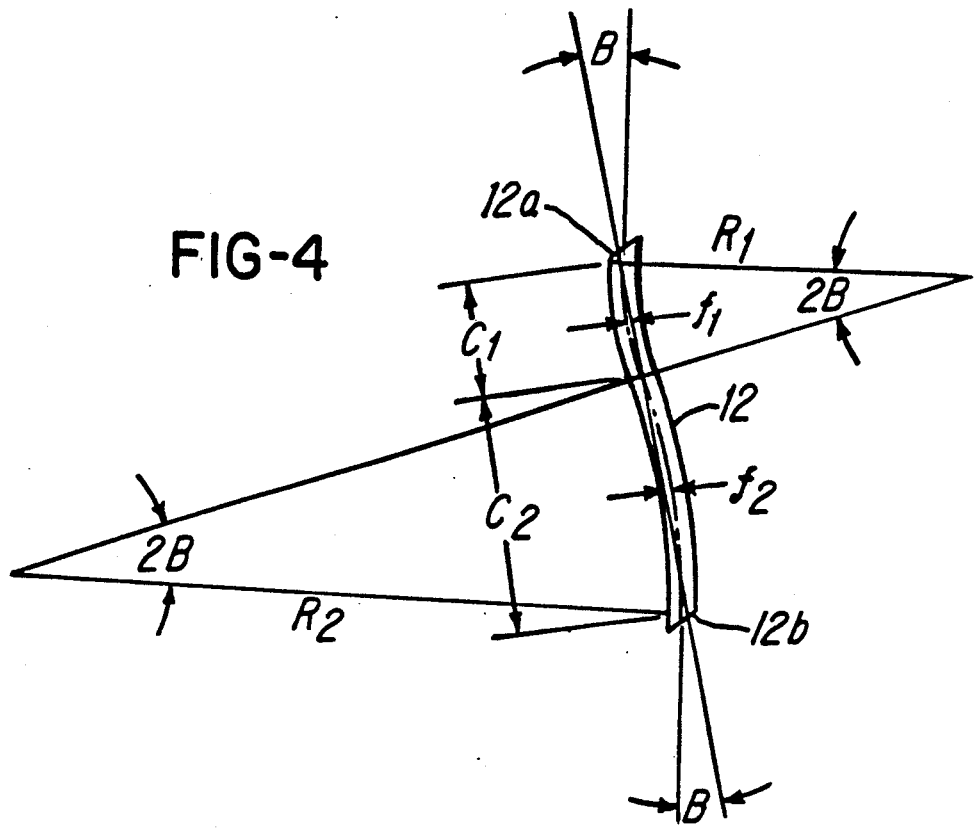
FIG. 4 shows an exploded or expanded view representing detailed features of one of the leaflets of the prosthetic heart valve shown in FIG. 3.

FIG. 1 is a plan view of a prosthetic heart valve V as seen from an upstream or top direction. A pair of leaflets 10 and 12 are housed within an annular shaped frame 13 also called means defining or forming an orifice 14. For the purposes of discussion, a bileaflet configuration is used. In this view, the leaflets 10, 12 are in the fully closed position to block the orifice 14 in the frame 13.

The leaflets 10, 12 are constrained within the orifice 14 such that they are free to rotate about pivots P, P' mounted in the frame 13 and also are eccentrically mounted. The leaflets 10, 12 are shown in the fully open position from an upstream or top direction in FIG. 2. The leaflets 10, 12 have leading edges 10a and 12a that are bevelled to permit a reasonably tight seal at the contact surface between the leaflets 10, 12 and a peripheral inner surface 13a of the orifice 14 formed in the frame 13 when the leaflets 10, 12 are fully closed.

The prosthetic heart valve V is shown in cross-section in FIG. 3, with the leaflets 10, 12 fully open. The leaflets 10, 12 have trailing edges 10b and 12b that are also bevelled to permit a reasonably tight seal with the inner wall surface 13a of the orifice 14 in the frame 13.

The leaflets 10, 12 are bicurved in shape. This is demonstrated in FIG. 4, where the leaflet 12 is shown in an exploded or expanded schematic view to show further details of the features thereof improved in accordance with the present invention. The leaflet 12 is generated from sections of two intersecting circular arcs. The arcs can be thought of as being generated from two contacting right circular cylinders. The radii of curvature of the two arcs are $R_1$ and $R_2$. These radii are not equal. The two arcs sweep two chords, defined as $c_1$ and $c_2$. Each arc forms a small semicircular shaped airfoil with cambers $f_1$ and $f_2$. The two arcs intersect at the point where the two generating circles contact. As the two generating circles (or cylinders) contact at only one point, the two chords are parallel. Further, this contact point can be constructed from the intersection of a line coincident with the two cords and a line through the center of both generating circles. Tangents to the leading and trailing edges of the two arcs are parallel. Thus, the apparent angle of attack of the leaflet is B, which is the angle between the forward flow and a line coincident with the two chords. As the two generating circles contact at only one point, the two sectors formed from the two chords $c_1$ and $c_2$ are both 2B. The mathematical relationship between the chords, cambers, radii, and angle of attack is $$f_i = 0.5 c_i \tan(B/2) \quad (1)$$

and $$R_i = (c_i^2 + 4f_i^2)/(8f_i). \quad (2)$$

Mode of Operation

The artificial heart valve V is shown in FIG. 1, prior to the onset of the forward flow phase. As noted previously, for purposes of discussion, a bileaflet configuration is used. The leaflets 10 and 12 are eccentrically constrained within the confines of the orifice 14 in the frame 13 such that they are both in the fully closed position.

As the forward flow phase begins, hemodynamic forces (due to the eccentric mounting) on the leaflets 10 and 12 cause them to rotate within the orifice 14 in the frame 13 to the fully open position, as shown in FIGS. 2 and 3. The forward flow phase passes easily through the open leaflets 10 and 12. They are fixed in this position by their constraints within the orifice 14 in the frame 13 and the hemodynamic forces.

When the forward flow phase is complete, the hemodynamic forces change and the leaflets 10 an 12 again rotate within the confines of the orifice 14 in the frame 13, until they come to rest in the fully closed position as shown in FIG. 1. They are again fixed in this position by their constraints within the orifice 14 in the frame 13 and the hemodynamic forces. Reasonably tight seals are formed between the mating surfaces of the leaflets 10, 12 at their leading edges 10a and 12a. Similar seals are formed from the bevelling at the trailing edges 10b and 12b of the leaflets 10, 12 and the inner wall surface 13a of the orifice 14 in the frame 13, as shown in FIG. 3.

The leaflets 10, 12 remain in the closed position throughout the regurgitant flow phase. As another cardiac cycle begins, the leaflets again open and the above process is repeated, causing essentially unidirectional flow through the prosthesis.

The unique shape of the leaflet 12 is illustrated in FIG. 4. As the forward flow phase enters the orifice 14 in the frame 13, the fluid particles approach the leading edge 12a of the leaflet 12. These particles easily travel along the initial length of the arc (chord $c_1$), because the tangent to the arc at the leading edge is parallel to the forward flow. The fluid particles then proceed, decelerating on the convex side (facing the centerline of the orifice) and accelerating on the concave side (facing the inner wall surface 13a of the orifice 14). As the flow is decelerating on the convex side, the potential for separation exists.

However, the ratio of the chords $c_1/c_2$ is less than one and before significant separation can occur, the curvature begins to change in the opposite direction. The change in curvature occurs at the intersection point of the two generating circles. As the intersection occurs at only one part, the curvatures of both arcs are identical at the transition point, yielding a smooth transition between the two arcs. This causes the flow to remain attached to the leaflet as it enters the second curved region of the leaflet 12.

As the fluid particles progress, they now accelerate on the concave side (facing the centerline of the orifice 14). This change from deceleration to acceleration, on side of the leaflet 12 facing the centerline, causes a favorable pressure gradient, therefore, preventing separation. Furthermore, as the fluid particles reach the trailing edge 12b, they are released into the free stream in the same direction of the forward flow.

On the convex side (facing the inner wall surface 13a of the orifice 14), the flow still accelerates. This is because the effective flow area on this side of the leaflet 12 decreases as the particles travel the length of the leaflet 12. The reduction in effective flow is, of course, due to the angle of attack B of the leaflet 12. As the fluid particles reach the trailing edge 12b, they too are released into the free stream in the same direction as the forward flow. The fact that the trailing edge arc is concave facing the centerline of the orifice 14, will augment leaflet closure by virtue of its increased drag potential.

At the onset of the regurgitation flow phase, the leaflets 10 and 12 close and return to the position demonstrated in FIG. 1. During the process, a certain volume of fluid is displaced in the regurgitant flow direction, by virtue of the motion of the leaflets 10, 12. This volume of fluid, the closing reflux volume, depends on B (FIG. 4), via the Theorem of Pappus. However, since the leaflet is non-planar, less fluid is refluxed due to the cambers $f_1$ and $f_2$ (FIG. 4), when compared to a at leaflet. Furthermore, this effect is significantly increased as the camber ratio $f_2/f_1$ increases, which is possible (see FIG. 4 or equations (1) and (2)), only when the chord ratio $c_1/c_2$ decreases.

Figure 5:
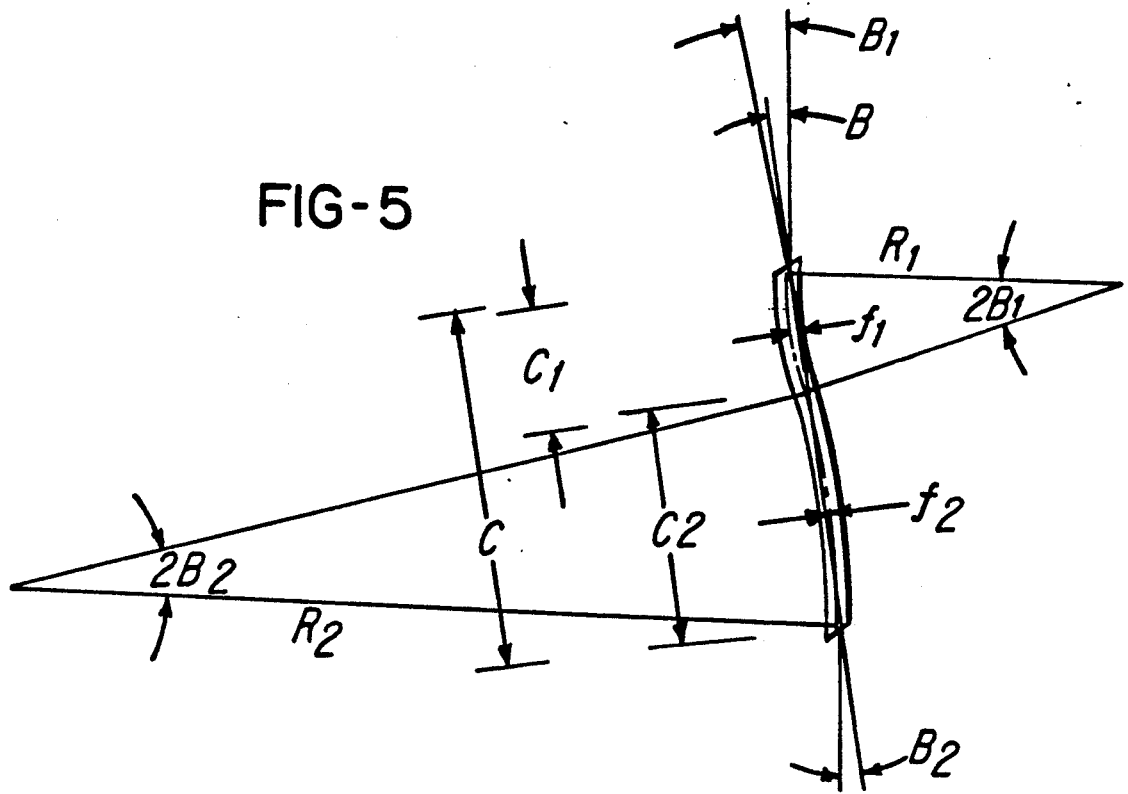
FIG. 5 shows an exploded or expanded view representing detailed features of one of the leaflets of an alternative embodiment of the prosthetic heart valve.

FIG. 5 shows an alternative embodiment of the artificial heart valve leaflet. This embodiment differs from the preferred embodiment in that the two generating circles intersect at more than one point. This causes the chords $c_1$ and $c_2$ to no longer be parallel, which then causes the effective angle of attack B to be smaller than B, which is the angle formed by the cords $c_1$ and $c_2$. The effective chord length c is no longer $c_1$ and $c_2$. The pertinent mathematical relationships are $$f_i = 0.5 c_i \tan(B_i/2), \quad (3)$$

$$R_i = (c_i^2 + 4f_i^2)/(8f_i), \quad (4)$$

$$c \sin(B) = c_1 \sin(B_1) + c_2 \sin(B_2), \quad (5)$$

and $$\cos(B - B_2) = (c_2^2 + c^2 - c_1^2)/(2c_2 c). \quad (6)$$

The general purpose of the present invention is to disclose a mechanical heart valve that can be used in persons meeting the generally accepted medical criteria for the replacement of their diseased native heart valves, or dysfunctional artificial heart valves (biological or mechanical) already implanted. The mechanical heart valve utilizes an annular shaped orifice and one or more bicurved leaflets.

According to the preferred embodiment of the present invention, the leaflet or leaflets are hinged to have pivots in the frame forming the orifice such that unidirectional flow occurs through the orifice.

A significant aspect of the improvement features of the present invention is the fact that the leaflets are formed from the intersection of two circular arcs. The radii of curvature of the two intersecting arcs are not equal. The generation from two simple circular arcs makes manufacturing easier.

Another significant aspect of the improvement features of the present invention is that the intersecting arcs are constructed such that tangents to the arcs at both the leading and trailing edges of the leaflet(s) are parallel to the forward flow. This general configuration markedly reduces the turbulence in the wake region of the leaflet(s) and realigns the flow at the trailing edge, thus reducing the work load on the heart.

A further significant aspect of the improvement features of the present invention is that the ratio of the chord of the leading edge arc to the chord of the trailing edge arc is less than one (1). This reduces separation effects by ensuring a predominantly accelerating flow through the orifice. This too reduces the work load on the heart.

An additional significant aspect of the improvement features of the present invention is that regurgitation effects can be significantly reduced. This is due to the unique bicurved shape, which reduces the closing reflux or regurgitant volume by permitting larger angles of attack via the nature of its non-planar shape and because the shape of the trailing edge reduces the closing time of the leaflet(s).

Additional drawing illustrations of the prosthetic heart valve of the present invention are provided in copending U.S. Ser. No. Des. 375,300-Reif filed June 30, 1989 concurrently herewith and incorporated herewith by reference thereto.

The present invention is, of course, in no way restricted to the specific disclosure of the specification and drawings, but also encompasses any modifications within the scope of the appended claims.

What I claim is:

1. A mechanical artificial heart valve comprising:
   a) one or more leaflets,
   b) means forming an annular shaped orifice,
   c) said leaflets being attached to said means forming the orifice, said attachment via a pivot being eccentrically hinged, d) said leaflets being bicurved in shape, said curvatures being formed by intersecting circular arcs, with which said circular arcs sweep two chords and each arc forms a small semi-circular shaped air foil with cambers, said two arcs intersecting where two generating circles contact and as the two generating circles contact, the two chords are other than parallel;

e) a tangent to an arc at a leading edge of said leaflets being parallel to forward flow during valve open positioning, f) a tangent to an arc at a trailing edge of said leaflets also being parallel to forward flow during valve open positioning, g) a ratio of the chord of the leading edge arc to the chord of trailing edge arc of said leaflets being definitely less than 1, and h) the forward flow through the heart valve remaining attached to the said leaflet because of the predominantly accelerating flow through the said orifice;

radii of curvatures of intersecting circular arcs being unequal; and two generating circles for a leaflet intersect at more than one point so that cords $c_1$ and $c_2$ are other than parallel to cause the effective angle of attack B to be other than equal to the angle formed by the chords $c_1$ and $c_2$.

2. A mechanical artificial heart valve in accordance with claim 1, wherein the effective chord length c forms a triangle with chords $c_1$ and $c_2$ and pertinent mathematical relationships are $$f_i = 0.5 c_i \tan(B_i/2),$$

$$R_i = (c_i^2 + 4f_i^2)/(8f_i),$$

$$c \sin(B) = c_1 \sin(B_1) + c_2 \sin(B_2),$$

and $$\cos(B - B_2) = (c_2^2 + c^2 - c_1^2)/(2 c_2 c).$$

3. A mechanical artificial heart valve in accordance with claim 2, wherein said leaflet includes edges lying in a single plane.

4. A mechanical artificial heart valve in accordance with claim 2, wherein said leaflet at least in part has a planar configuration and since ratio of the chords $c_1$ and $c_2$ is less than one and before significant separation effect can occur on one side of the leaflet, the curvature begins to change in an opposite direction thus to attain reduced separation effect with consequently smaller pressure losses, reduced regurgitation, and ease of manufacture.

* * * * *